(12) United States Patent
Tadin et al.

(10) Patent No.: US 7,617,068 B2
(45) Date of Patent: Nov. 10, 2009

(54) METHOD FOR DETERMINING RELATIVE MOBILITY OR REGIONS OF AN OBJECT

(75) Inventors: Tony Tadin, Woodside, CA (US); Arjen Sundman, Lake Oswego, OR (US)

(73) Assignee: Amfit, Inc., Vancouver, WA (US)

( * ) Notice: Subject to any disclaimer, the term of this patent is extended or adjusted under 35 U.S.C. 154(b) by 0 days.

(21) Appl. No.: 11/584,290

(22) Filed: Oct. 20, 2006

(65) Prior Publication Data

US 2008/0097720 A1 Apr. 24, 2008

(51) Int. Cl.
*G01B 5/20* (2006.01)
*G01B 5/207* (2006.01)
*G01B 7/28* (2006.01)
*G01B 7/287* (2006.01)

(52) U.S. Cl. .......................... 702/139; 356/2; 356/600; 356/601; 600/300; 600/587; 600/589; 702/138; 702/166; 702/167; 702/168

(58) Field of Classification Search .................. 73/104; 356/2, 388, 394, 600, 601; 382/100, 106, 382/108; 600/300, 587, 592; 702/1, 127, 702/138, 139, 166, 167, 168, 187, 189
See application file for complete search history.

(56) References Cited

U.S. PATENT DOCUMENTS

| | | | |
|---|---|---|---|
| 2,087,584 A | 7/1937 | Staudinger | 73/151 |
| 2,795,953 A | 6/1957 | Makowsky | 73/172 |
| 4,267,728 A | 5/1981 | Manley et al. | 73/172 |
| 4,814,661 A | 3/1989 | Ratzlaff et al. | 310/328 |
| 4,858,621 A | 8/1989 | Franks | 128/779 |
| 4,917,105 A | 4/1990 | Tiitola et al. | 128/779 |
| 5,088,503 A | 2/1992 | Seitz | 128/779 |
| 5,128,880 A | 7/1992 | White | 364/550 |
| 5,237,520 A | 8/1993 | White | 364/560 |
| 5,252,916 A * | 10/1993 | Swart | 324/757 |
| 5,341,819 A | 8/1994 | Hyvärinen | 128/779 |
| 5,471,405 A * | 11/1995 | Marsh | 702/41 |
| 5,678,448 A | 10/1997 | Fullen et al. | 73/172 |
| 5,800,364 A | 9/1998 | Glennie et al. | 600/592 |
| 5,941,835 A | 8/1999 | Sundman | 600/592 |
| 5,992,224 A * | 11/1999 | Weinhold et al. | 73/81 |
| 6,331,893 B1 | 12/2001 | Brown et al. | 356/601 |
| 6,546,356 B1 * | 4/2003 | Genest | 702/153 |
| 6,549,639 B1 * | 4/2003 | Genest | 382/100 |
| 6,637,275 B2 * | 10/2003 | Wu | 73/862.046 |
| 6,804,571 B2 | 10/2004 | Fullen et al. | 700/118 |
| 6,904,692 B2 * | 6/2005 | Tadin | 33/515 |
| 7,068,379 B2 * | 6/2006 | Sundman et al. | 356/601 |
| 7,434,459 B2 * | 10/2008 | Schmidt et al. | 73/172 |
| 2001/0047246 A1* | 11/2001 | Fullen et al. | 702/33 |
| 2003/0117371 A1* | 6/2003 | Roberts et al. | 345/156 |

(Continued)

*Primary Examiner*—Edward R Cosimano
(74) *Attorney, Agent, or Firm*—Ohlandt, Greeley, Ruggiero & Perle, L.L.P.

(57) ABSTRACT

A method for determining a mobility of foot comprising: measuring at least a portion of a shape of the foot under a first weight load; measuring the at least the portion of the shape of the foot under a second weight load; and comparing the measurement under the first weight load to the measurement under the second weight load, thereby determining a mobility of at least the portion of the foot.

33 Claims, 6 Drawing Sheets
(2 of 6 Drawing Sheet(s) Filed in Color)

U.S. PATENT DOCUMENTS

| | | | |
|---|---|---|---|
| 2003/0212506 A1 | 11/2003 | Sundman et al. | 702/40 |
| 2004/0138849 A1* | 7/2004 | Schmidt et al. | 702/127 |
| 2004/0148089 A1* | 7/2004 | Schmidt et al. | 701/124 |
| 2005/0022407 A1* | 2/2005 | Tadin | 33/515 |
| 2007/0115093 A1* | 5/2007 | Kurtz | 340/5.52 |
| 2008/0083416 A1* | 4/2008 | Xia et al. | 132/200 |
| 2008/0120044 A1* | 5/2008 | Hoysan | 702/41 |

* cited by examiner

METHOD FOR DETERMINING RELATIVE MOBILITY OR REGIONS OF AN OBJECT

BACKGROUND OF THE INVENTION

1. Field of the Invention

The present disclosure relates to object contour measurements, and more particularly, to methods for determining mobility of different regions of a foot.

2. Description of the Related Art

Mobility, i.e., a difference in the position of a structure of a foot between loaded and unloaded states, is an important measurement, especially for determining the support needs of a person. The mobility of various areas of the foot vary from person to person. A relatively more mobile foot will flex more during ambulation (walking) than the more rigid foot. A foot with more mobility is also more likely to pronate excessively. This can result in foot instability and undo fatigue, which may result in stress, foot, knee and/or back injury.

The relative mobility of a foot is therefore important information when trying to understand any particular foot's needs for support in gait. This can be an especially powerful piece of information when trying to determine the proper footwear for a given foot. In addition, this information is helpful in determining what type of foot orthotic and the amount of support needed, in the range of rigid to semi-flexible to soft. A retailer with knowledge of the customer's mobility would be able to properly recommend a shoe and presumably have a sales advantage.

There is a need for an apparatus and method for determining the relative mobility of various areas of an object such as a foot.

SUMMARY OF THE INVENTION

A method for determining a mobility of an object, e.g., a foot, comprising: measuring at least a portion of a shape of the object under a first weight load; measuring the at least the portion of the shape of the object under a second weight load; and comparing the measurement under the first weight load to the measurement under the second weight load, thereby determining a mobility of at least the portion of the object.

Another embodiment includes a method for determining a mobility of an object, comprising: measuring a first elevation from a reference plane of at least one location on an object under a first weight load; measuring a second elevation from the reference plane of the at least one location on the object under a second weight load; and determining a mobility of the object at the at least one location based on a difference between the first elevation and the second elevation.

The reference plane is preferably a surface platform.

Optimally, mobility is determined by the formula:

(Object Elevation at Initial Loaded State at (X,Y))−
(Object Elevation at Second Loaded State at
(X,Y))=(Mobility of Foot at (X,Y))

The elevation measurement is taken along an axis perpendicular to the reference plane.

The method further comprises displaying the mobility to a user, customer and/or physician. The displaying preferably includes providing a visual indication of mobility characteristics across a surface of the object.

The method further comprises wherein at least one location is a plurality of locations arrayed on a surface of the object.

The method wherein each the measuring step uses a measurement system selected from the group consisting of: one or more gauge pins that contact a surface of the object, and one or more swing sensor arms.

Optionally, the method wherein each the measuring step uses an optical scanner that incorporates a light source to determine the elevation, wherein the light source is selected from the group consisting of: a structured light, a laser light source and a combination thereof.

Alternatively, the method wherein the measuring step uses a pattern that is adhered or conformed to the foot and is captured by an imaging device (e.g., camera, chemical or digital) and postprocessing to evaluate the surface of the foot. One such pattern is applied via a sock with stripe patterns on its which utilizes a camera to evaluate the shape of the stripes to determine the shape of the contour of the foot. Another embodiment, involves the use of a hand-held digital camera for creating a grid of sorts without a sock along with a lens having a built-in grid capability for measuring the foots angulation and geometry.

Alternatively, the method wherein each the measuring step uses an optical scanner that includes a camera to evaluate the surface of the foot.

The method wherein each the measuring step uses a pressure measurement to characterize the surface of the foot.

The method further comprising: comparing the mobility of the at least one location of the object with a mobility of a reference object.

The method further comprising designing, based on the mobility, a medical treatment selected from the group consisting of: an orthotic intervention and a surgical procedure.

The method further comprising selecting, based on the mobility, a support device selected from the group consisting of: footwear and an insole.

The method further comprising transmitting the visual indication of mobility characteristics to a remote location.

A method of evaluating the effectiveness of a proposed orthotic intervention, comprising: determining a desired mobility of at least a portion of a foot; placing the foot in a position that creates the desired mobility; determining an actual mobility of at least the portion of the foot by measuring at least a portion of a shape of the foot under a first weight load; measuring the at least the portion of the shape of the foot under a second weight load; and comparing the measurement under the first weight load to the measurement under the second weight load, thereby determining the actual mobility of at least the portion of the foot; and comparing the actual mobility to the desired mobility to determine whether the desired mobility has been achieved.

Optimally, the foot is placed in the position by inserting a mechanical support under a selected portion of the foot.

A computer-readable medium having computer-executable instructions for executing a method comprising the steps of: measuring a first elevation from a reference plane of at least one location on an object under a first weight load; measuring a second elevation from the reference plane of the at least one location on the object under a second weight load; and determining a mobility of the object at the at least one location based on a difference between the first elevation and the second elevation.

The computer-readable medium wherein the method further comprises displaying the mobility to a user, customer and/or physician.

The computer-readable medium wherein the step of displaying includes displaying information selected from the group consisting of: the first elevation, the second elevation, the mobility, and any combination thereof.

The computer-readable medium wherein the method further comprising designing a corrective treatment based on the mobility, and displaying the corrective treatment to a user.

The computer-readable medium wherein the corrective treatment is selected from the group consisting of: an orthotic intervention, a support device, and a surgical procedure.

BRIEF DESCRIPTION OF THE DRAWINGS

The patent or application file contains at least one drawing executed in color. Copies of thie patent or patent application publication with color drawing(s) will be provided by the Office upon request and payment of the necessary fee.

DETAILED DESCRIPTION OF THE PREFERRED EMBODIMENT

The present disclosure provides an apparatus and method for determining a mobility of an object such as a foot by measuring an elevation or height of one or more points on the plantar surface of the foot, for example under the medial longitudinal arch, in at least two states: i) an unloaded or minimally loaded state and ii) a fully loaded state. The difference in the heights of each point in the loaded and unloaded states is used as an indicator of the midfoot mobility. It is the objective of the present disclosure to set forth a method of using these measurements in establishing relative mobility of various areas of the foot.

Figure 1:
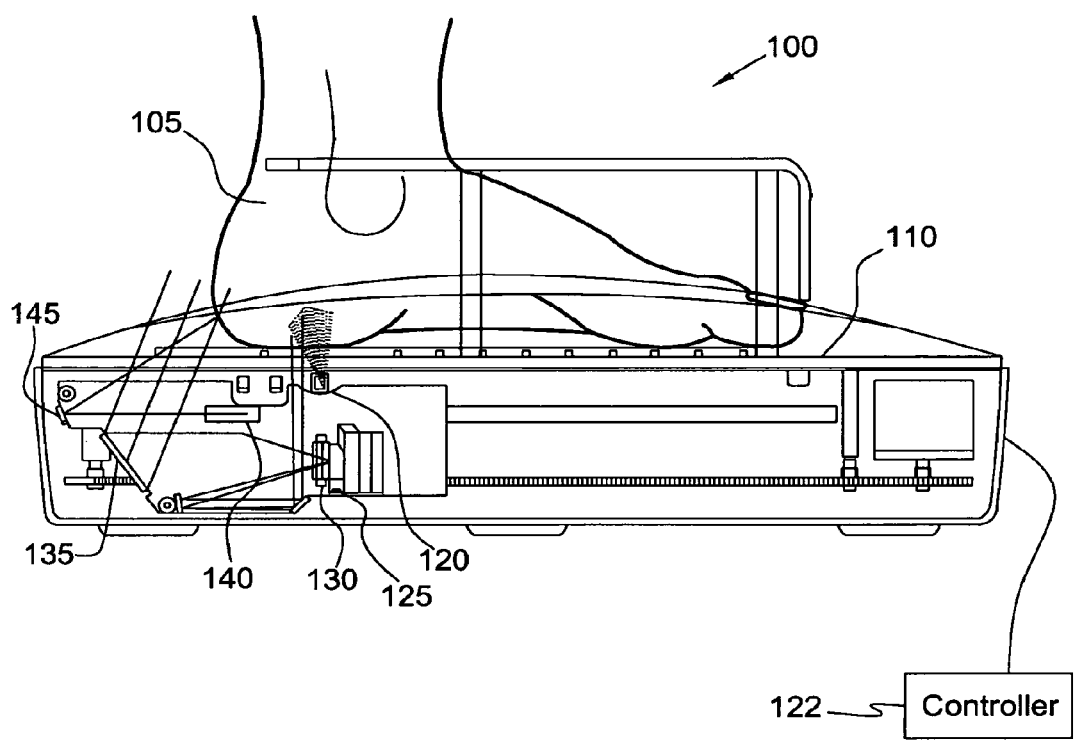
FIG. 1 is a side view of an exemplary device for measuring the contours of an object, namely an optical contour digitizer.
Figure 2:
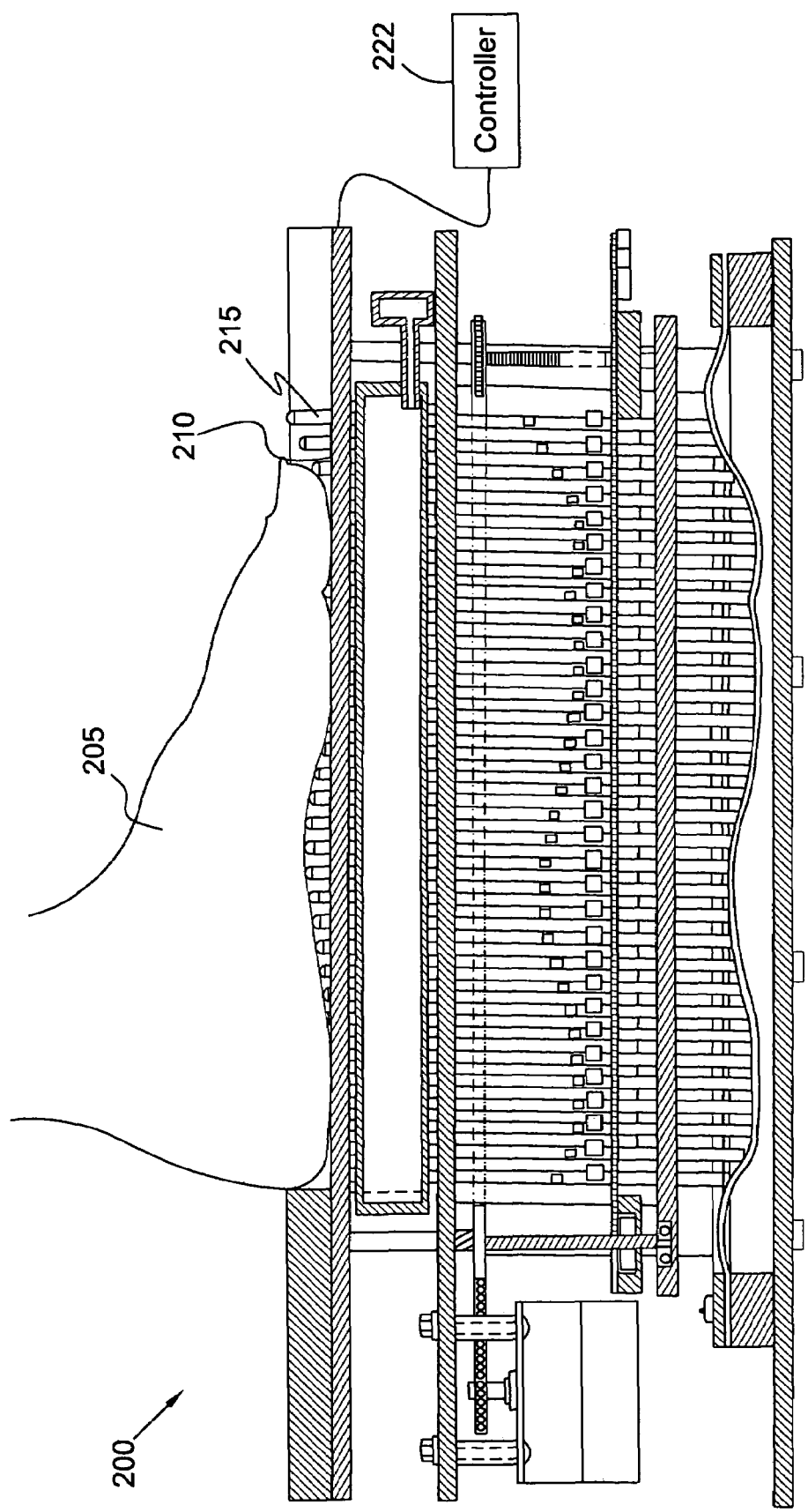
FIG. 2 is a cross-sectional side view of an exemplary device for measuring the contours of an object, namely a pin digitizer with a foot placed thereon.

Referring to the drawings and, in particular, FIGS. 1 and 2, examples of devices useful in measuring the contour of an object are shown. Although the present disclosure is described in the context of a human foot, any object can be measured using the following devices and methods, particularly any objects or body parts that exhibit deformation when loaded.

FIG. 1 shows an optical contour digitizer 100 for measuring a contour of a foot 105. Digitizer 100 includes a transparent plate 110 and a carriage assembly that can be moved along an axis parallel to plate 110. The carriage assembly includes a support 120 that carries a camera 125, a red pass filter 130, an image mirror 135, laser emitter 140, and laser mirror 145.

In operation, the carriage assembly is moved in a left-to-right direction along plate 110. Laser 140 transmits its emission against mirror 145 and through transparent plate 110 onto the subject surface of foot 105. An image of the surface is transmitted through transparent plate 110 onto image mirror 135, through red pass filter 130, and is viewed and captured by camera 125. The structure and operation of optical contour digitizer 100 is further described in U.S. patent application Ser. No. 10/407,925, now U.S. Pat. No. 7,068,379, which is incorporated by reference herein.

FIG. 2 shows a pin digitizer 200 for measuring the contours of a foot 205. Digitizer 200 includes a surface 210 having an array of apertures (not shown), and an array of gauge pins 215. In operation, foot 205 is placed on surface 210, and pins 215 are urged upwardly through the apertures in surface 210. The upward motion of pins 215 is stopped when pins 215 contact the surface of the underside of foot 205, and pins 215 cannot overcome the normal force with which the surface of foot 205 placed on surface 210 exerts downwardly on surface 210 and pins 215. Gauge pins 215 are optionally locked in place, and the change in elevation of each gauge pin 215 is determined. The position of gauge pins 215 can be determined using mechanical, electromechanical, optical, or a number of techniques and processes. The structure and operation of digitizer 200 is further described in U.S. patent application Ser. No. 10/871,556, which issued as U.S. Pat. No. 6,904,692, which is incorporated by reference herein.

The devices described above in conjunction with FIGS. 1 and 2 are purely exemplary. Any device that can take contour measurements or elevation measurements of an object may be suitable for use with the methods provided herein.

Figure 3:
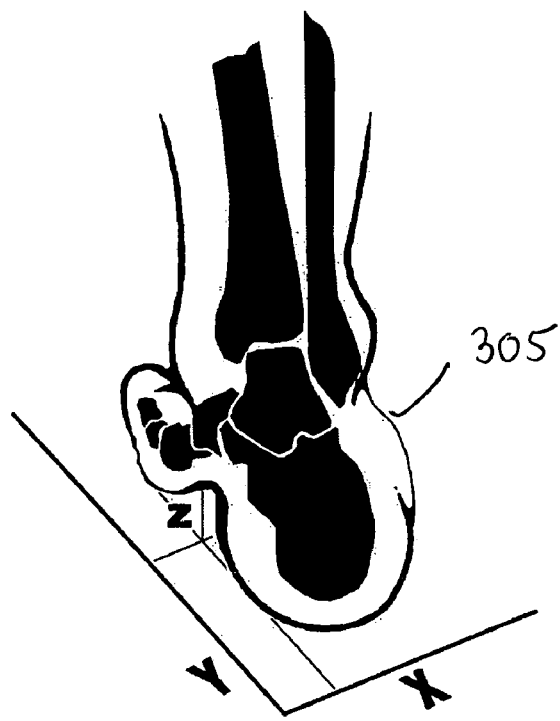
FIG. 3 is a posterior schematic view of a foot on an X/Y plane in an unloaded state.

FIG. 3 shows a posterior schematic view of a foot 305 on an X/Y plane in an unloaded state. The Z vector indicates the elevation of a point on the underside of the foot, in this case the arch, as measured at a given X/Y point.

Figure 4:
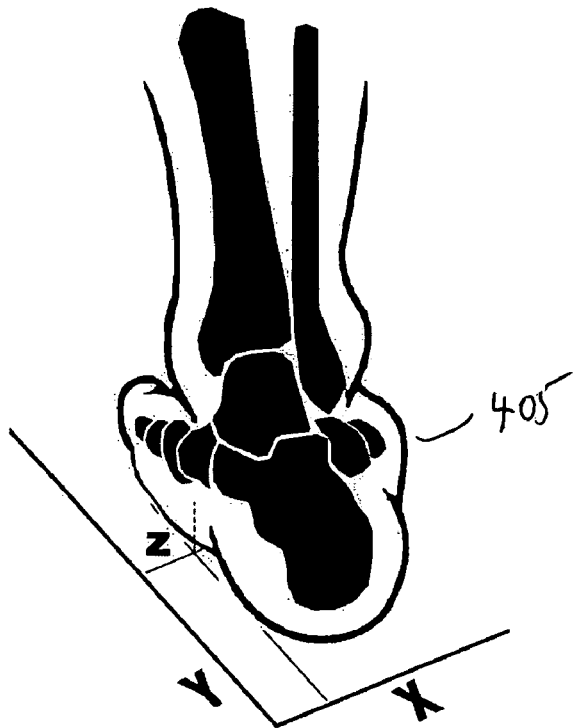
FIG. 4 is a posterior schematic view of a foot on an X/Y plane in a loaded state.

FIG. 4 shows a similar posterior schematic view of a foot 405 on an X/Y plane in a loaded state. The Z vector, located at the same X/Y position as shown in FIG. 3, is significantly shorter. This is a function of the mobility of the subject foot. Some feet will show greater or lesser differences. The variables that effect the observed differences include: arch height, weight, and age.

In a preferred method, one or more points are measured under the plantar aspect of a foot, preferably under the medial longitudinal arch. This measurement is preferably done at or about the apex of the arch and medial of the longitudinal midline of the foot. The measurement may also be performed under the medial or lateral heel to evaluate mobility of the calcaneous or the forefoot.

At least two measurements are performed at each point on the subject surface of the foot. A first measurement is performed at a point with the foot unloaded or minimally loaded, and a second measurement is performed in that same point with the foot supporting a selected loading. In a preferred embodiment, the second measurement may be performed with the foot "fully loaded", i.e., as supporting full body weight. The load on the foot may be any selected amount of weight, or any load representing various positions of the body, such as sitting, crouching, etc. It may also be desirable in some cases to measure the foot with all the body's weight on one foot or in an overloaded state to see what the foot does under extreme stress. Although two measurements are described for each point, additional measurements may be taken for each point at various load amounts.

There are many existing technologies to take a measurement of this sort. These technologies include optical scanning, utilizing light such as laser light, and reflected or structured light, and contact digitizing, where one or more gauge pins contact the subject surface and a linear measurement is made at each gauge pin's location. Examples of these technologies are discussed above. Additional technologies include: i) an array of sensor arms, e.g., swing arms, which are translated along an axis whose radial position can be used to evaluate elevation, and ii) impression foam or other shape-memory materials, where two impression are made of the foot and the resulting impressions are measured. One could also make a fully manual measurement of the arch or a simple mechanism can be devised to give an indication of the arch height and mobility.

In a preferred embodiment, a contact digitizer such as gauge pin digitizer 200 is used to make the measurements. A contact digitizer is ideally suited to this type of measurement as it has the ability to support the foot during measurement, has a built-in datum surface (i.e., its top plate), is highly accurate, and is able to provide closely correlated data points in the two weight states required.

For the initial measurement, the unloaded or minimally loaded foot is placed on top surface 210 of contact digitizer 200. Gauge pins 215 are urged upwards against the undersurface of the foot. The relative heights of each of gauge pins 215 is noted. This is preferably done using a processor to note and store each gauge pin's height. For the second measurement, the subject foot resting on surface 210 has normal body weight applied to it. Gauge pins 215 are once again urged upwards against the undersurface of the foot and the relative heights noted.

After data has been collected, at least two data sets result. A first data set includes height or elevation measurements of one or more points, i.e., locations, on the underside of the foot in an unloaded or minimally loaded state. A second data set includes height measurements of one or more points on the underside of the foot in a selected or fully loaded state. Each point represented in the first data set should also be represented in the second data set.

In a preferred embodiment, a large array of data points are measured, in order to have a complete picture of the elevation of each area of the foot. This can be accomplished using, for example, digitizer 200. In another embodiment, an optical digitizer, such as digitizer 100, can provide a continuous measurement of elevation over all areas of the foot.

Depending on the measurement methodology, the data sets may contain as few as one or many numbers indicating the relative heights of the foot in one or more locations. The contact digitizer records the heights over a wide area of the plantar aspect of the foot. Preferably, each data set represents an array of points on the underside of the foot, so that an accurate determination of the deformation of the foot at various points can be determined. By analyzing the differences between the data from the unloaded and loaded foot, a determination of the relative mobility of the foot in the region analyzed can be made.

In one embodiment, if the mobility of the arch of a given foot needs to be determined, the foot is measured twice, i.e., once in an unloaded state and once in a loaded state. The elevations of the sample point(s) under the arch are compared. The resulting difference is then compared against a data set of previously measured feet or an algorithm based on known foot dynamics to make a determination of the relative foot mobility in that foot's arch region, compared to a "normal" foot or compared to a foot having selected characteristics. Similarly, the data point(s) could be under the medial or lateral heel to evaluate mobility of the calcaneous or the forefoot to evaluate forefoot varus/valgus in various weight states.

The apparatus used in the method described herein may include a controller 122, 222 for taking measurements, calculating the data set from each set of measurements, and/or providing mobility data to a user. The controller 122, 222 preferably includes a computing platform, such as a personal computer, a mainframe computer, or any other type of computing platform that may be provisioned with a memory device, a CPU or microprocessor device, and several I/O ports. Software instructions for carrying out the methods described herein are stored in the memory device, and executed by the CPU or microprocessor. The software is capable of developing data which can be used to determine the corrective amount required as a function of the foots mobility. The controller 122, 222 may also include a display or other device for providing mobility information. In another embodiment, mobility data and/or the display may be transmitted to a remote user.

Mobility information may be provided to the user as raw data, or as a data set, such as in spreadsheet form, showing each height measurement and indicating the measurement location and load state. The data set may alternatively only include calculated mobility measurements, i.e., differences between heights of a point in various load states, for each measured point on an object's surface. The data set may also be provided to the user in various visual forms, such as is described below.

Figure 5:
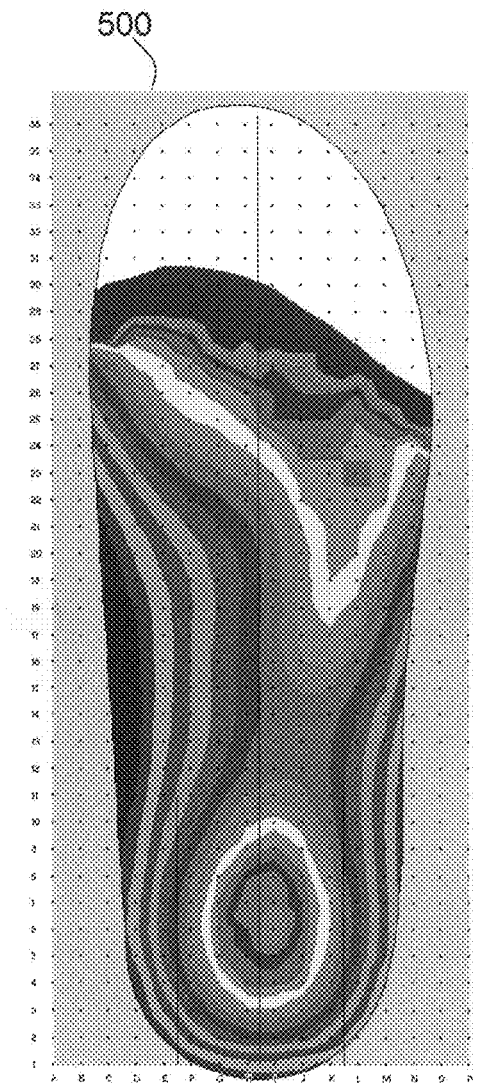
FIG. 5 is a topographical display of an unloaded foot.
Figure 6:
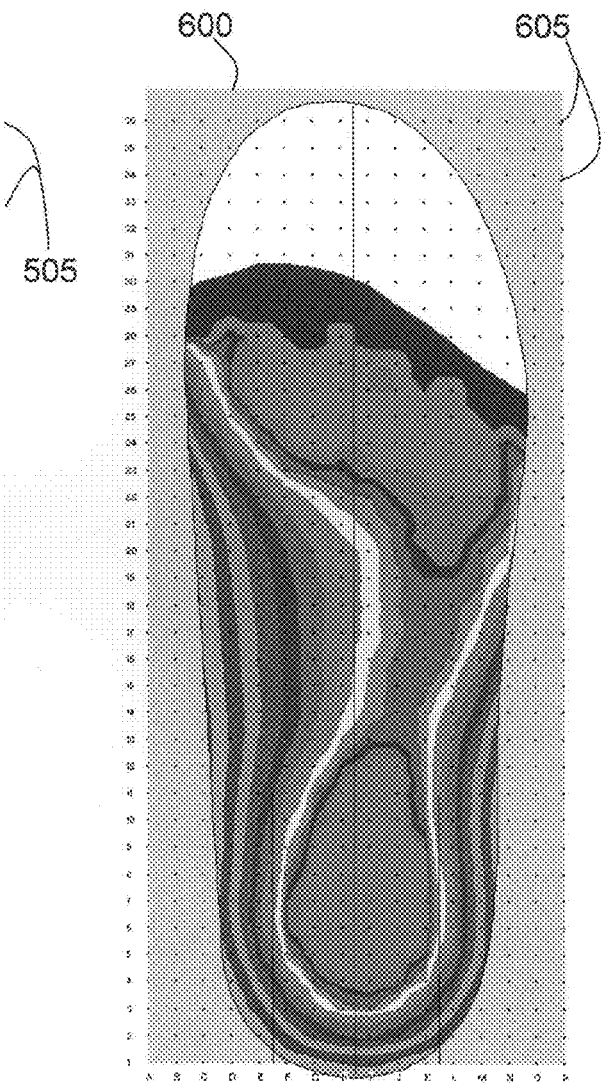
FIG. 6 is a topographical display of a foot in a loaded state.
Figure 7:
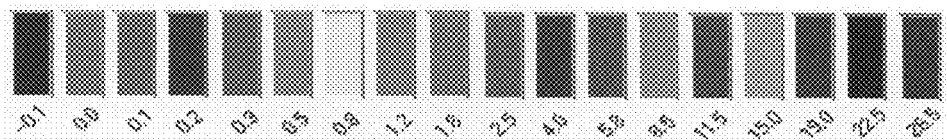
FIG. 7 is a legend that shows the range of elevation represented in FIGS. 5 and 6.

FIG. 5 shows an elevation display 500, as a result of a computer scan of an unloaded foot, with the data represented in a topographical format. FIG. 6 shows an elevation display 600 of the same foot in a loaded state. FIG. 7 is a color legend that shows the range of elevation represented in FIGS. 5 and 6, in millimeters. FIGS. 5 and 6 also have a superimposed array of dots 505 and 605 that are referenced along the x axis by letters and along the Y axis by numbers. Comparing the two displays provides a clear indication of the changed state of this subject foot in a loaded or unloaded state.

Comparing the elevation in a number of locations is illustrative of the analysis methodology and the information that can be gleaned from it. Looking at the elevation in FIG. 5 at location E-16 shows an elevation of approximately 17 mm. The same location in FIG. 6 (in a loaded state) shows an elevation of approximately 8 mm. The simple formula:

$$(\text{Unloaded Foot Elevation at } (X,Y)) - (\text{Loaded Foot Elevation at } (X,Y)) = (\text{Mobility of Foot at } (X,Y))$$

can be used to indicate foot function, malfunction and provide a wealth of information useful to the design of interventions to address various foot maladies especially for young children. This result can be compared with mobility data on a reference foot to determine whether support may be needed or helpful in this location of the foot. With early foot orthotic intervention the foot can realign itself.

A similar analysis at location E-26 in FIG. 5 versus FIG. 6 shows a significantly altered elevation pattern. In the unloaded state, the elevation of the foot at this point is approximately 1.2 mm. In the loaded state, the elevation of the foot at this point is 0 mm. This information indicates the need for posting (additional support) under the medial forefoot to achieve a proper gait. In the case presented here, a medial forefoot post of approximately 2 degrees to address a forefoot varus is indicated.

Other regions of the foot can also reveal useful diagnostic information by comparing the loaded or semi-loaded foot's contour information against the same foot in an unloaded state. Some of these include: heel pronation, heel supination, Charcot foot, heel spur, dropped metatarsal head, rigid foot issues, and forefoot varus or valgus. Each of these conditions can be helped by using the information revealed by this process to design an effective orthotic intervention.

Figure 8:
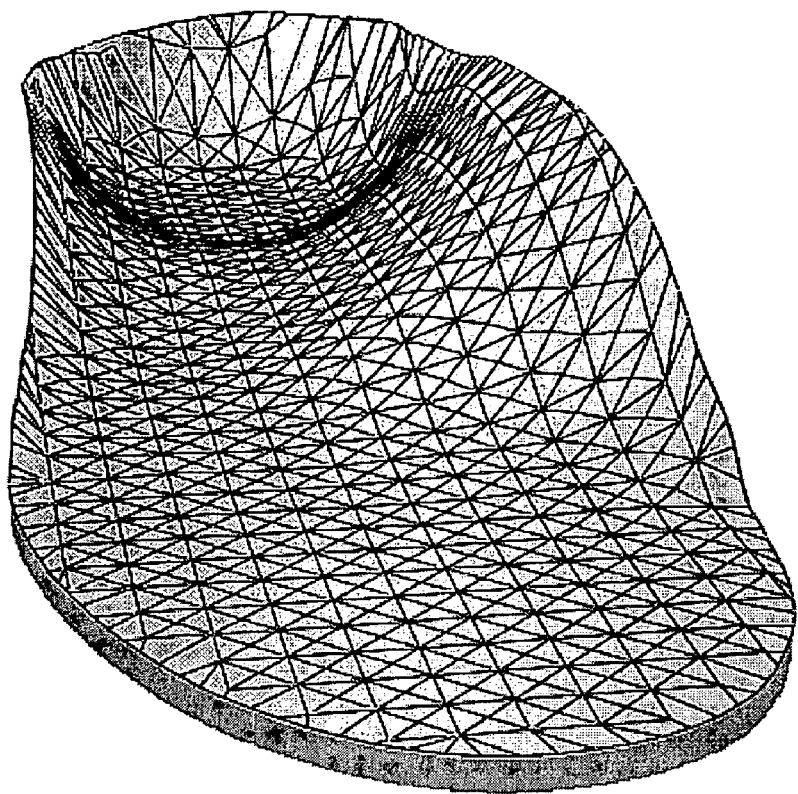
FIG. 8 is a computer rendering of the negative of the unloaded foot of FIG. 5, as viewed from the anterior of the foot.
Figure 9:
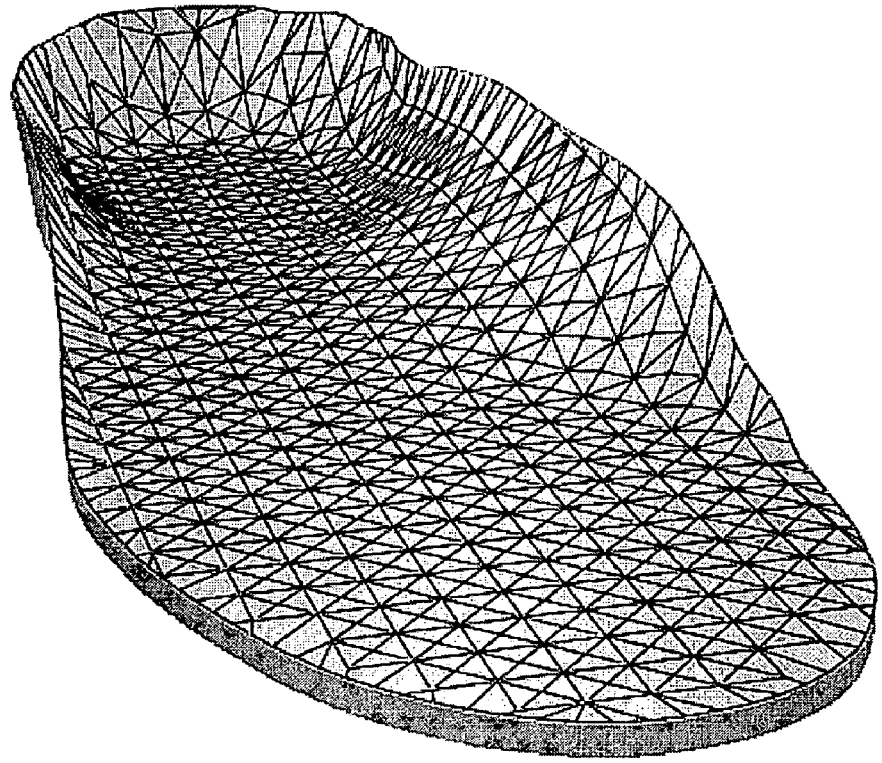
FIG. 9 is a computer rendering of the negative of the loaded foot of FIG. 6, as viewed from the anterior of the foot.

FIG. 8 is a computer rendering of the negative of an unloaded foot as viewed from the anterior of the foot. FIG. 9 shows the same foot in a loaded state. It is easy to see the changes in the arch height and shape as well as the posting evident in the medial forefoot.

In another embodiment, elevation display 500, or mobility data in any other form, may be transmitted to a remote user. For example, display 500 or measurement information may be displayed to an off-site doctor or foot specialist for consultation. This may be accomplished via a teleconference, or by transmitting mobility data via a network such as an intranet or the internet, or by e-mail. Such remote transmission is useful, as a user may be able to receive advice from experts regarding orthotic or other medical intervention without the cost and delay associated with having additional live consultations or with sending a patient to numerous specialists.

Figure 10:
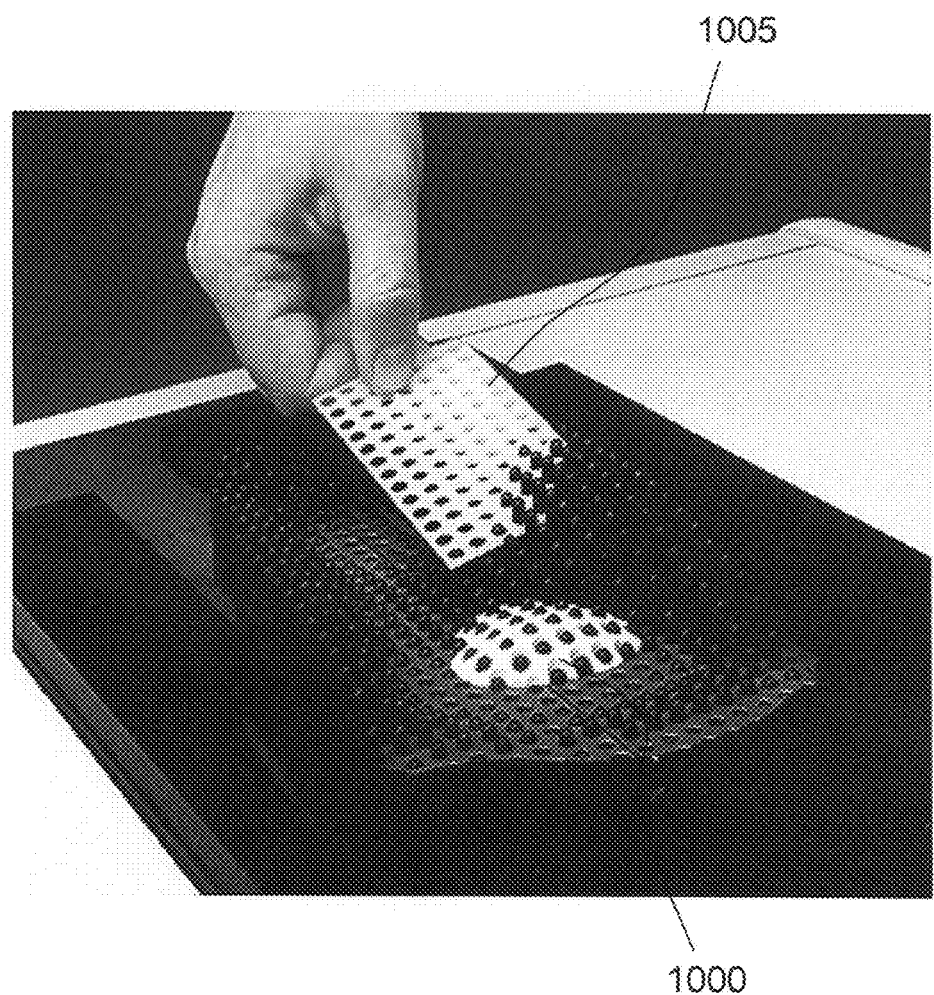
FIG. 10 is an exemplary gauge pin digitizer with an appliance in place to correct a foot's position.

FIG. 10 shows a picture of a gauge pin digitizer 1000 with an appliance 1005 in place to correct the foot's position. FIG. 10 shows the position of the gauge pins with the appliance in-place and the gauge pins elevated as if they were contacting the foot. By measuring the gauge pins in this state, it can be determined if the proposed appliance is addressing the excess mobility as desired.

The method may also be enhanced by including pressure measurements at various points on the underside of the foot. These measurements may be useful in providing information as to the pressure distribution on the surfaces of the foot that contact a surface, especially when the foot is loaded. In one example, top surface 210 of contact digitizer 200 may incorporate an array of pressure sensors embedded or resting on top surface 210. Pressure sensors would only register a reading for those surfaces in contact with top surface 210. The pressure readings may be displayed similarly to elevation display 500. The pressure readings may be displayed separately from elevation readings such as in elevation display 500, or may be incorporated into elevation display 500. For example, those areas showing a 0.00 or −0.01 elevation may be given pressure indications, so that a user can easily see the pressure distribution over the areas having no elevation. Although pressure measurements alone have drawbacks, because the are a two-dimensional measurement and therefore cannot measure mobility, such as arch drop mobility, pressure measurements can be useful as an enhancement to elevation mobility measurements.

A method is provided that includes the measuring and analyzing elevation data described above. The method may also include utilizing the resulting characterization of the foot's mobility to 1) indicate the need for orthotic intervention, and 2) provide suggestions on the nature of that intervention. For example, it can be determined from the exemplary elevation data shown in FIGS. 5-9 that the forefoot of this subject needs forefoot medial posting. The elevation difference in the forefoot is used in this example to indicate the amount of the posting required to restore the foot's proper functioning. In this example, the forefoot should have posting on the order or 2 degrees medially. Similarly other elevation analysis can be used to indicate orthotic interventions like: hindfoot medial and lateral posting, heel spur relief, metatarsal head relief, metatarsal arch support (a.k.a. metatarsal pad or metatarsal bar) and medial and lateral forefoot posting.

The method may also include the additional step of providing validation of an adjustment being made to the foot. For example, if used in conjunction with a gauge pin measurement device such as device 1000 of FIG. 10, an adjustment appliance, such as adjustment device 1005, can be placed between the foot and the reference plane. This device would be selected to correct for the mobility that is being derived by this technology. By doing an additional measurement of the foot with the appliance in-place, it can be determined if the foot stays in a position more like the unloaded foot. In another embodiment, the software includes a capability for a user to simulate the inclusion of orthotic interventions or other supports, and determine the mobility of various locations of the foot.

For example, the user may input a selected orthotic support or otherwise input the dimensions of an orthotic support. Based on this input, software that is run by the processor will modify the mobility data. The modified mobility data may then be displayed, such as in a format similar to that shown in FIGS. 5-9, to a user to allow the user to observe the effect that the orthotic support has on the mobility of the foot.

The method may also be used in conjunction with a video teleconference or still images to assist in diagnosing and designing interventions for patients remotely. These images could be transmitted in any of a number of generally available technologies including, but not limited to, I/P, optical, and wireless.

For example, a user may take mobility measurements of a patient's foot as described above. These measurements may be transmitted to and displayed to a medical professional or expert who may be in a location remote to that of the patient and user. The patient can then get the benefit of the expertise of one or more professionals without having to physically travel to that professional to have mobility measured. Furthermore, the user in this embodiment need only know how to operate the system to take mobility measurement data.

When the mobility measurement data is transmitted to an expert, the expert may analyze the data to determine what type of intervention is recommended, if any. The software allows the expert (or any other user) to simulate various orthotic supports and display the mobility of the foot with that support. This feature allows the expert to test various supports and determine the ideal supports to recommend. A video camera may also be incorporated in the system described above to take images of the foot in various loaded states, so that the expert can visualize the position and loading of the foot that corresponds with received mobility measurement data.

Alternatively, the present disclosure comprises a method for determining a mobility of an object, such as a foot, comprising: measuring at least a portion of a shape of the object under a first weight load; measuring the at least the portion of the shape of the object under a second weight load, wherein the measuring of the object under either or both of the first and second weight loads utilizes a pattern that is adhered or conformed to the object and wherein the patterns are captured by an imaging device; and comparing the patterns measured from the first and second weight loads, thereby determining a mobility of at least the portion of the object.

Preferably, the imaging device is at least one device selected from the group consisting of: camera, chemical and digital.

The pattern is applied via a sock with a stripe pattern disposed thereon and wherein the imaging device is evaluates the shape of the stripes to determine the shape of the contour of the object.

Another embodiment of the present disclosure comprises a method for determining a mobility of an object, comprising: measuring at least a portion of a shape of the object under a first weight load; measuring the at least the portion of the shape of the object under a second weight load, wherein the measuring of the object under either or both of the first and second weight loads is carried out via an imaging device comprising a grid for measuring the patterns of the object under a first and second weight load, and wherein the patterns are captured by the imaging device; and comparing the patterns measured from the first and second weight loads, thereby determining a mobility of at least the portion of the object.

It should be understood that various alternatives, combinations and modifications of the teachings described herein could be devised by those skilled in the art. The present disclosure is intended to embrace all such alternatives, modifications and variances that fall within the scope of the appended claims.

What is claimed is:

1. A method for determining a mobility of an object, comprising:
    measuring at least a portion of a shape of said object under a first weight load using a device;
    measuring said at least said portion of said shape of said object under a second weight load using the device; and
    comparing said measurement under said first weight load to said measurement under said second weight load, thereby determining a mobility of at least said portion of said object.

2. The method of claim 1, wherein said object is a foot.

3. A method for determining a mobility of an object, comprising:
    measuring a first elevation from a reference plane of at least one location on an object under a first weight load using a device;
    measuring a second elevation from said reference plane of said at least one location on said object under a second weight load using the device; and
    determining a mobility of said object at said at least one location based on a difference between said first elevation and said second elevation.

4. The method of claim 3, wherein said reference plane is a surface platform.

5. The method of claim 3, wherein said object is a foot.

6. The method of claim 3, where said mobility is determined by the formula:

(Object Elevation at Initial Loaded State at $(X,Y)$)–
(Object Elevation at Second Loaded State at $(X,Y)$)=(Mobility of Foot at $(X,Y)$).

7. The method of claim 3, wherein said elevation measurement is taken along an axis perpendicular to said reference plane.

8. The method of claim 3, wherein said at least one location is a plurality of locations arrayed on a surface of said object.

9. The method of claim 3, wherein each said measuring step uses a measurement system selected from the group consisting of: one or more gauge pins that contact a surface of said object, and one or more swing sensor arms.

10. The method of claim 3, wherein each said measuring step uses an optical scanner that incorporates a light source to determine said elevation, wherein said light source is selected from the group consisting of: a structured light, a laser light source and a combination thereof.

11. The method of claim 3, wherein each said measuring step uses an optical scanner that includes a camera to evaluate the surface of the foot.

12. The method of claim 3, where each said measuring step uses a pressure measurement to characterize the surface of the foot.

13. The method of claim 3, further comprising:
    comparing said mobility of said at least one location of said object with a mobility of a reference object.

14. The method of claim 3, further comprising designing, based on said mobility, a medical treatment selected from the group consisting of: an orthotic intervention and a surgical procedure.

15. The method of claim 3, further comprising selecting, based on said mobility, a support device selected from the group consisting of: footwear and an insole.

16. The method of claim 3, further comprising displaying said mobility to a user, customer and/or physician.

17. The method of claim 16, wherein said displaying includes providing a visual indication of mobility characteristics across a surface of said object.

18. The method of claim 16, further comprising transmitting said visual indication of mobility characteristics to a remote location.

19. A method of evaluating the effectiveness of a proposed orthotic intervention, comprising:
    determining a desired mobility of at least a portion of a foot;
    placing said foot in a position that creates said desired mobility;
    determining an actual mobility of at least said portion of said foot by measuring at least a portion of a shape of said foot under a first weight load; measuring said at least said portion of said shape of said foot under a second weight load; and comparing said measurement under said first weight load to said measurement under said second weight load, thereby determining said actual mobility of at least said portion of said foot; and
    comparing said actual mobility to said desired mobility to determine whether said desired mobility has been achieved.

20. The method of claim 19, wherein said foot is placed in said position by inserting a mechanical support under a selected portion of said foot.

21. A computer-readable medium having computer-executable instructions for instructing a machine to execute a method comprising the steps of:
    measuring a first elevation from a reference plane of at least one location on an object under a first weight load;
    measuring a second elevation from said reference plane of said at least one location on said object under a second weight load; and
    determining a mobility of said object at said at least one location based on a difference between said first elevation and said second elevation.

22. The computer-readable medium of claim 21, wherein said method further comprises displaying said mobility to a user, customer and/or physician.

23. The computer-readable medium of claim 22, wherein said step of displaying includes displaying information selected from the group consisting of: said first elevation, said second elevation, said mobility, and any combination thereof.

24. The computer-readable medium of claim 21, wherein said method further comprising designing a corrective treatment based on said mobility, and displaying said corrective treatment to a user.

25. The computer-readable medium of claim 24, wherein said corrective treatment is selected from the group consisting of: an orthotic intervention and a surgical procedure.

26. A method for determining a mobility of an object, comprising:
    measuring at least a portion of a shape of said object under a first weight load using a device;
    measuring said at least said portion of said shape of said object under a second weight load using the device, wherein said measuring of said object under either or both of said first and second weight loads utilizes a pattern that is adhered or conformed to said object and wherein said patterns are captured by an imaging device; and comparing said patterns measured from said first and second weight loads, thereby determining a mobility of at least said portion of said object.

27. The method of claim 26, wherein said object is a foot.

28. The method of claim 26, wherein said imaging device is at least one device selected from the group consisting of: camera, chemical and digital.

29. The method of claim 26, wherein said pattern is applied via a sock with a stripe pattern disposed thereon and wherein said imaging device is evaluates the shape of said stripes to determine the shape of the contour of said object.

30. A method for determining a mobility of an object, comprising:

measuring at least a portion of a shape of said object under a first weight load using a device;

measuring said at least said portion of said shape of said object under a second weight load using the device, wherein said measuring of said object under either or both of said first and second weight loads is carried out via an imaging device comprising a grid for measuring the patterns of said object under a first and second weight load, and wherein said patterns are captured by said imaging device; and comparing said patterns measured from said first and second weight loads, thereby determining a mobility of at least said portion of said object.

31. The method of claim 30 wherein said object is a foot.

32. The method of claim 30, wherein said imaging device is at least one device selected from the group consisting of: camera, chemical and digital.

33. The method according to claims 1 or 3, or 26 or 30, wherein said device is one of a contact pin digitizer, an impression foam of shape memory materials, an array of sensor arms, and an optical scanning device.

* * * * *